US010335025B2

(12) United States Patent
Rifai et al.

(10) Patent No.: US 10,335,025 B2
(45) Date of Patent: Jul. 2, 2019

(54) SYSTEM AND METHOD FOR THE TRAINING OF HEAD MOVEMENTS

(71) Applicant: Carl Zeiss Vision International GmbH, Aalen (DE)

(72) Inventors: Katharina Rifai, Tuebingen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 127 days.

(21) Appl. No.: 15/292,949

(22) Filed: Oct. 13, 2016

(65) Prior Publication Data
US 2017/0156587 A1 Jun. 8, 2017

(30) Foreign Application Priority Data
Oct. 13, 2015 (DE) .................. 10 2015 219 868

(51) Int. Cl.
*A61B 3/10* (2006.01)
*A61B 5/11* (2006.01)
*A61B 3/00* (2006.01)
*A61B 5/00* (2006.01)
*G02C 7/02* (2006.01)

(52) U.S. Cl.
CPC .............. *A61B 3/10* (2013.01); *A61B 3/0008* (2013.01); *A61B 3/0016* (2013.01); *A61B 5/11* (2013.01); *A61B 5/6814* (2013.01); *G02C 7/025* (2013.01)

(58) Field of Classification Search
CPC ........ G02C 7/025; G02C 7/027; G02C 7/028; G02C 7/061; G02C 13/002; G02C 13/003; G02C 13/005; G02B 27/00; A61B 3/0008; A61B 3/0016; A61B 3/028; A61B 3/10; A61B 3/11; A61B 3/113; A61B 3/117; A61B 5/0077; A61B 5/11; A61B 5/742; A61B 5/1116; A61B 5/1128; A61B 5/6803; A61B 5/6814
USPC ..... 351/159.74, 204–209, 246; 600/476, 595
See application file for complete search history.

(56) References Cited

U.S. PATENT DOCUMENTS

| 6,827,443 | B2 | 12/2004 | Fisher et al. | |
|---|---|---|---|---|
| 2003/0107707 | A1* | 6/2003 | Fisher | A61B 3/113 351/159.74 |
| 2007/0229761 | A1* | 10/2007 | Gimenez Carol | A61B 3/113 351/209 |
| 2012/0182521 | A1 | 7/2012 | Kubitza et al. | |

* cited by examiner

*Primary Examiner* — Mustak Choudhury
(74) *Attorney, Agent, or Firm* — Walter Ottesen, P.A.

(57) ABSTRACT

The invention relates to a system and to a method for training head movements of a person. Visual stimuli are generated with a visual stimulus generation device for a left and/or right eye of the person. Head movements of the person are captured with a measurement device. The head movement of the person captured with respect to a generated visual stimulus is assessed in a computational unit. Assessment information that is dependent on the assessment of the head movement captured with respect to a generated visual stimulus is then provided for the person with an output device.

17 Claims, 6 Drawing Sheets

SYSTEM AND METHOD FOR THE TRAINING OF HEAD MOVEMENTS

CROSS REFERENCE TO RELATED APPLICATION

This application claims priority of German patent application no. 10 2015 219 868.5, filed Oct. 13, 2015, the entire content of which is incorporated herein by reference.

FIELD OF THE INVENTION

The invention relates to a system and to a method for training head movements of a person. The invention additionally relates to a computer program for such a system and such a method. The invention also extends to a computer program product having program code for training head movements of a person on a computational unit.

BACKGROUND OF THE INVENTION

The training of head movements of a person is of interest in particular for wearing progressive spectacles. A progressive lens is here understood to mean a spectacle lens with different refractive powers for distance correction and near correction of defective vision and generally also presbyopia. In contrast to single-vision lenses, it is possible with a progressive lens to view sharply a distance range which is specified in a distance point and near point via the refractive power of the progressive lens. However, the visual impression perceived by a spectacle wearer through the progressive lenses of progressive spectacles depends significantly on the head movement behaviour of said wearer. The visual impression for a spectacle wearer becomes increasingly clear, the better he is able, using head movements, to ensure that the viewing direction in each case penetrates a region of the spectacle lens that is adapted to a desired object distance. Wearing progressive spectacles therefore generally requires that the spectacle wearer changes his head movement behavior as compared to seeing without glasses or seeing with single-vision lenses or with contact lenses. This must be adapted to the geometry of the near zone, the distance zone and the progression channels of the progressive lenses. Adapting the head movement behavior to progressive spectacles is, however, difficult for a spectacle wearer because in progressive lenses, changing the viewing direction without a corresponding head movement causes a blurred visual impression, and the spectacle wearer does not notice that the cause for this visual impression is an inadequate head movement. This is because the information of the blurred visual impression contains no information for the spectacle wearer regarding the direction of head movements that improve the visual impression. In particular, the mere information of a blurred visual impression does not contain any information as to how the spectacle wearer must change his head movement so that he sees a clear picture. The result of this is that the statistic of natural head movements of the spectacle wearer is crucial for whether the adaptation of the head movement behavior to progressive spectacles is a success or a failure.

U.S. 2012/018251 A1 describes an apparatus for capturing head postures of a subject in order to ascertain herefrom a preferred head posture so that for the correction of centering data, an ascertained deviation of a habitual head posture from an actual head posture can be taken into consideration.

U.S. Pat. No. 6,827,443 B2 discloses an apparatus and a method for specifying one or more lens designs which are adapted to the viewing behavior of a subject. To this end, in particular head movements of the subject are captured.

SUMMARY OF THE INVENTION

It is an object of the invention to provide a system and a method for training head movements of a person with which the person can learn head movements which are of advantage in particular for him or her.

In order to train the head movements of a person, the invention proposes to generate visual stimuli for the person and to capture the head movement of the person after the visual stimulus has been generated. The person's head movement captured with respect to the generated visual stimulus is then assessed so as to provide information that is dependent on the assessment of the head movement captured with respect to the generated visual stimulus. It is a concept of the invention in particular to train a spectacle wearer with this, such that the spectacle wearer learns to adapt their head movement behavior to progressive spectacles. However, it is also possible with the invention to train persons who suffer from neck and/or back pain with the objective of improving their head mobility and of increasing the movement range for the head movements.

One embodiment of a system according to the invention for training head movements of a person contains a visual stimulus generation device for generating visual stimuli for a left and/or a right eye of the person, and a measurement device for capturing head movements from a starting head posture to an end head posture of the person. There is an assessment device for assessing the head movement from the starting head posture to the end head posture of the person, which movement is captured with respect to a generated visual stimulus and which generates assessment information that is dependent on the head movement captured with respect to the generated visual stimulus and qualifies the quality of the head movement, and an output device for providing the assessment information for the person.

The invention is in particular based on the finding that the head movements of spectacle wearers who have a head movement behavior which is adapted to progressive spectacles are faster, take place over a shorter time period and with a larger movement range and moreover also start earlier compared to the head movements of persons who do not wear progressive spectacles.

For the training of the head movements of a person, the invention proposes in particular to provide feedback information for the person which goes beyond right/wrong information, and the person thus receives an assessment with respect to a captured head movement, for example a relative assessment of the head movement, such as for example better or worse, or an assessment of the head movement in intermediate stages, for example the intermediate stage "good," the intermediate stage "a little better," and the intermediate stage "excellent."

A system according to the invention for training head movements of a person therefore contains a visual stimulus generation device for generating visual stimuli for a left and/or a right eye of the person. Present in the system is furthermore a measurement device for capturing head movements of the person. The system has an assessment device for assessing the head movement of the person that is captured with respect to a generated visual stimulus, and has an output device for providing assessment information for the person that is dependent on the assessment of the head movement captured with respect to a generated visual stimulus.

The assessment device in the system is here preferably configured in the form of a computational unit, which contains a computer program for assessing the head movement of the person captured with respect to a generated visual stimulus. It is a concept of the invention in particular for the computer program to ascertain the assessment information by comparing the captured head movement with a predetermined head movement that is ascertained with respect to the generated visual stimulus, and to output it to the output device. Here, the computer program can determine the predetermined head movement with respect to the generated visual stimulus by way of reading a data set stored in a data memory. It is advantageous if the computer program ascertains the predetermined head movement on the basis of a model which assigns a predetermined head movement to a visual stimulus. It is of particular advantage when the model takes into consideration individual spectacle lens adaptation parameters for the person. For example, the model can take into account one or more spectacle lens adaptation parameters from the group comprising frame dimensions, interpupillary distance, centration distance, corneal vertex distance, near reference point, distance reference point, refractive power, addition and width of the progression channel. It is possible in this way to teach a person visual behavior that is advantageous for wearing progressive spectacles. Alternatively or additionally, it is also possible, however, to merely positively assess an enlargement, an acceleration or the earlier initiation of a head movement on the basis of a generated visual stimulus.

The visual stimulus generation device in a system according to the invention can be configured for example in the form of a screen or in the form of a head-mounted display (HMD) or in the form of a tablet PC or in the form of a light source assembly or in the form of a light pattern projection device. The measurement device can have a camera, alternatively or additionally a position sensor arranged on the head of the person and/or a solid angle sensor and/or an acceleration sensor for capturing head movements. The device for providing the assessment information in the system can generate, for example, an acoustic signal and/or a visual signal and/or a mechanical vibration signal for the person and/or a virtual reality which is perceivable by the person. It is also a concept of the invention to permit analysis of the head movements of a person with a system according to the invention.

A method according to the invention for training head movements of a person comprises the following steps: generating a visual stimulus for a left and/or right eye of the person; capturing a movement of the head of the person on the basis of the generated visual stimulus; assessing the movement of the head of the person captured with respect to the generated visual stimulus; and providing assessment information for the person that is dependent on the assessment of the movement of the head of the person captured with respect to the generated visual stimulus. The assessment information can be determined here by comparing the captured movement of the head with a predetermined head movement ascertained with respect to the generated visual stimulus. In particular, the assessment information in the method according to the invention can be provided in the form of an acoustic signal and/or in the form of a visual signal and/or in the form of a mechanical vibration signal and/or in the form of a virtual reality.

In one embodiment of the method according to the invention, the following steps are provided for training head movements of a person:
generating a visual stimulus for a left and/or right eye of the person,
capturing a movement of the head of the person from a starting head posture to an end head posture on the basis of the generated visual stimulus,
assessing the movement of the head of the person captured with respect to the generated visual stimulus, and generating assessment information that is dependent on the generated visual stimulus and on the head movement captured with respect to the generated visual stimulus and qualifies the quality of the head movement, and
providing the assessment information for the person.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
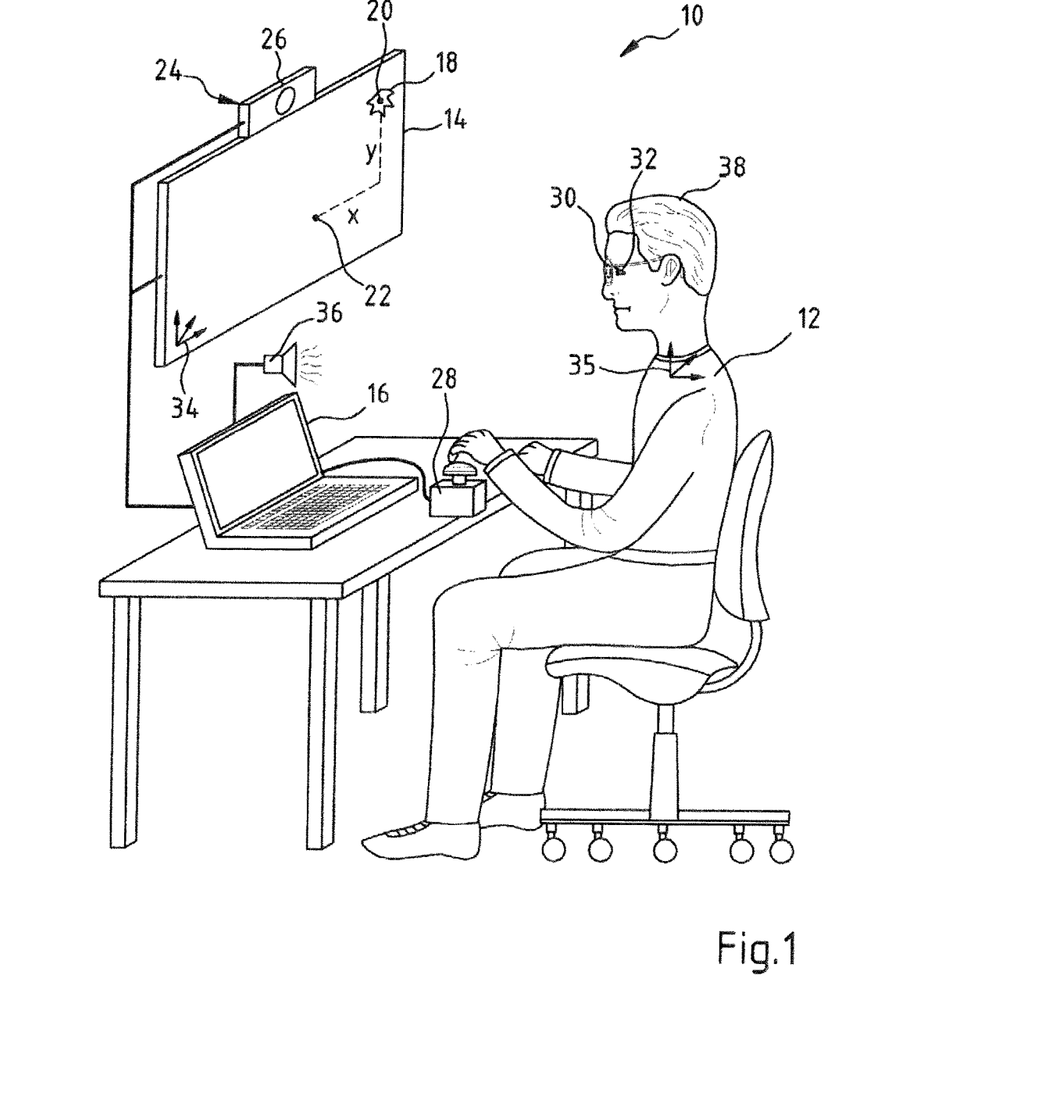
FIG. 1 is a first system for training head movements of a person.

The system 10 shown in FIG. 1 for training head movements of a person 12 is a head movement training system. The system 10 has a visual stimulus generation device 14 in the form of a screen. This screen is connected to a computational unit 16 which contains a computer program with an image generating routine in order to display for the person 12 on the screen in succession visual stimuli 18 whose location 20 with respect to the center 22 of the screen meets a random principle. The visual stimuli 18 displayed on the screen are presented here in the form of a bright, star-shaped pattern against a dark background.

In the system 10, there is a measurement device 24 for capturing the movement of the head 38 of the person 12 on the basis of a visual stimulus which is displayed to the person 12 by the visual stimulus generation device 14. The measurement device 24 has a camera 26, which is connected to the computational unit 16. In order to capture in the system 10 head movements of the person 12, the computer program in the computation unit 16 contains an image processing routine which can ascertain, by means of image evaluation, a movement of the head 38 of the person 12 from a starting head posture to an end head posture, where the person 12 moves the head 38 on the basis of a displayed visual stimulus 18.

The system 10 has an input interface 28 which enables the person 12 or a further person looking after the person 12 to trigger the display of a visual stimulus 18 at a position 20 on the screen that is specified according to a random principle.

Upon triggering the display of a visual stimulus 18 at the input interface 28, the visual stimulus 18 is displayed on the screen. At the same time, the head movement of the person 12 is captured by the measurement device 24 over a time interval \t which is settable at the input interface 28.

The head movement of the person 12 captured with the measurement device 24 is then assessed in the computational unit 16. The computer program in the computational unit 16 to this end contains an assessment routine. For assessing the head movement of the person 12, the assessment routine compares a value for the head movement of the person 12 which is favorable for the displayed visual stimulus 18 with a value for the head movement that is assigned to the visual stimulus 18. As a value for the head movement, the assessment routine takes into consideration a displacement of the center of rotation 30, 30' of the left and the right eye 32, 32' of the person 12 in a coordinate system 35 which is fixed with respect to the person and is referenced with respect to a coordinate system 34 of the screen.

On the basis of this comparison the assessment routine generates feedback information for the person 12 with the information content "good head movement," "excellent head movement," and "insufficient head movement."

For displaying the feedback information ascertained with the assessment routine in the computational unit 16, the computational unit 16 is connected to an output device 36 in the form of an acoustic signal generator which generates an acoustic indication signal with different volumes for the feedback information "good head movement," "excellent head movement," and "insufficient head movement." The volume for the indication of the feedback information "good head movement" is chosen here such that the test subject can clearly hear this signal. The volume for indicating the feedback information "excellent head movement" is comparatively louder, and the volume for indicating the feedback information "insufficient head movement" is lower. Alternatively or additionally it is possible to vary the pitch for different items of feedback information or to generate an unpleasant sound as feedback information for an "insufficient head movement" and a pleasant sound as feedback information for a "good head movement."

Figure 2:
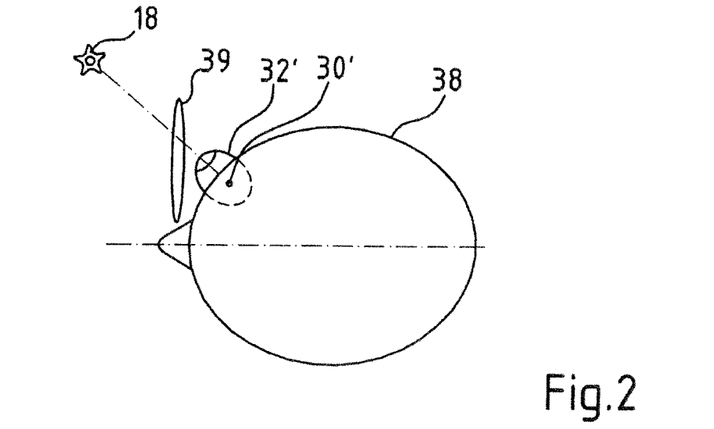
FIG. 2 is a visual stimulus and the head of a first person.

FIG. 2 shows a visual stimulus 18 and an associated first head movement of the person 12 during training with the system 10 for training head movements, illustrated in FIG. 1, during viewing using a progressive lens 39. The head 38 of the person 12 is here shown in a top view from above. The viewing direction of the person 12 here penetrates the progressive lens 39 eccentrically with a deviation from the progressive lens progression channel. The visual impression perceived by the person 12 is therefore distorted in this viewing direction.

Figure 3:
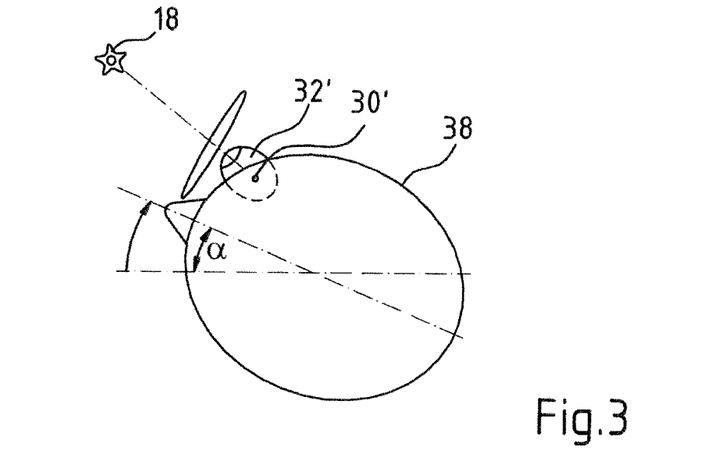
FIG. 3 is a visual stimulus and a head movement of the first person.
Figure 4:
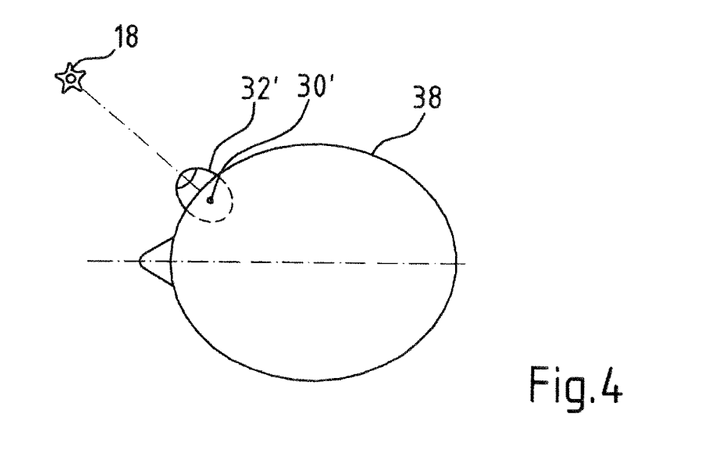
FIG. 4 is a visual stimulus and the head of a person without vision aid.

By contrast, FIG. 3 shows the visual stimulus 18 and an associated first head movement of the person 12 by rotating the head 38 about the head rotation angle corresponding to a head movement which is favorable for good viewing with the progressive lens 39. A person 12 must learn this head movement because, as can be seen in FIG. 4, the head posture of FIG. 2 corresponds to a natural head posture of a person 12 who does not require a vision aid for sharp viewing.

Figure 5:
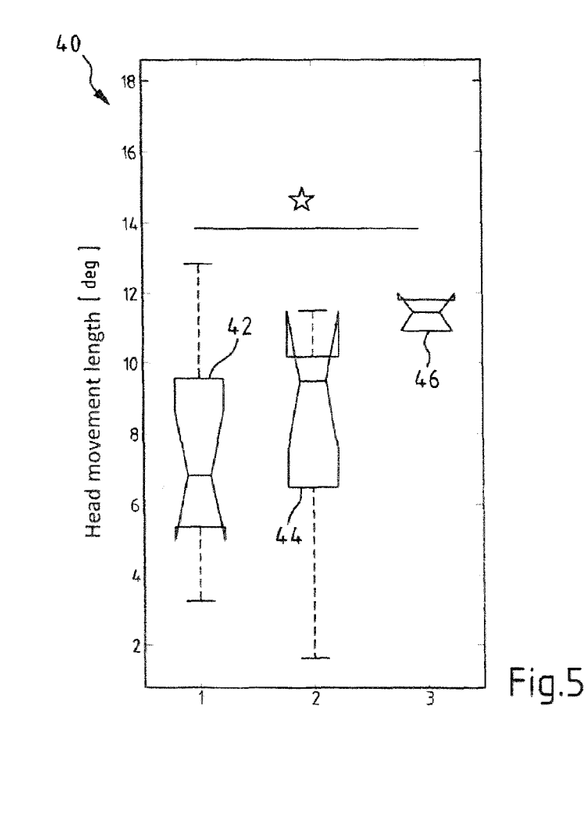
FIG. 5 is a diagram relating to statistical data regarding the length of the head movement triggered by a visual stimulus in persons wearing progressive spectacles and persons who do not wear progressive spectacles.

FIG. 5 shows a diagram 40 with statistical data with respect to the length of the head movement triggered by a visual stimulus 18 in persons wearing progressive spectacles and persons who do not wear progressive spectacles. Graph 42 shows a typical distribution of the length of head movements in ° [deg] in persons who do not wear progressive spectacles. Graph 44 visualizes a typical distribution of the head movement of persons wearing spectacles with progressive lenses with weak addition. The graph 46 in diagram 40 visualizes a typical distribution of the head movement in persons who wear spectacles with progressive lenses with strong addition.

Figure 6:
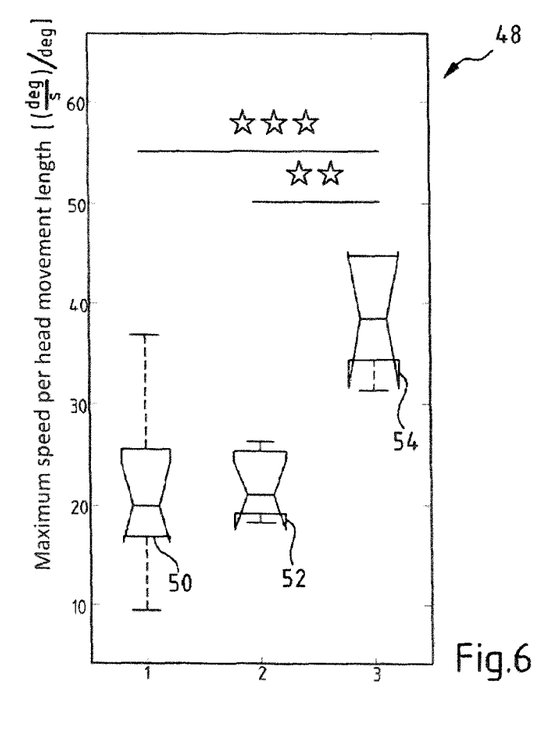
FIG. 6 is a diagram relating to statistical data regarding the maximum speed of the head movement triggered by a visual stimulus in persons wearing progressive spectacles and persons who do not wear progressive spectacles.

FIG. 6 is a diagram 48 with statistical data with respect to the maximum speed in (°/s) [deg/s] with respect to the length of the head movement in ° [deg] of a head movement triggered by a visual stimulus 18. Graph 50 shows a typical distribution of the speed of the head movement of persons who do not wear progressive spectacles. Graph 52 visualizes a typical distribution of the speed of the head movement of persons who wear spectacles with progressive lenses with weak addition. The graph 54 in the diagram 48 visualizes a typical distribution of the speed of the head movement of persons who wear spectacles with progressive lenses with strong addition.

Figure 7:
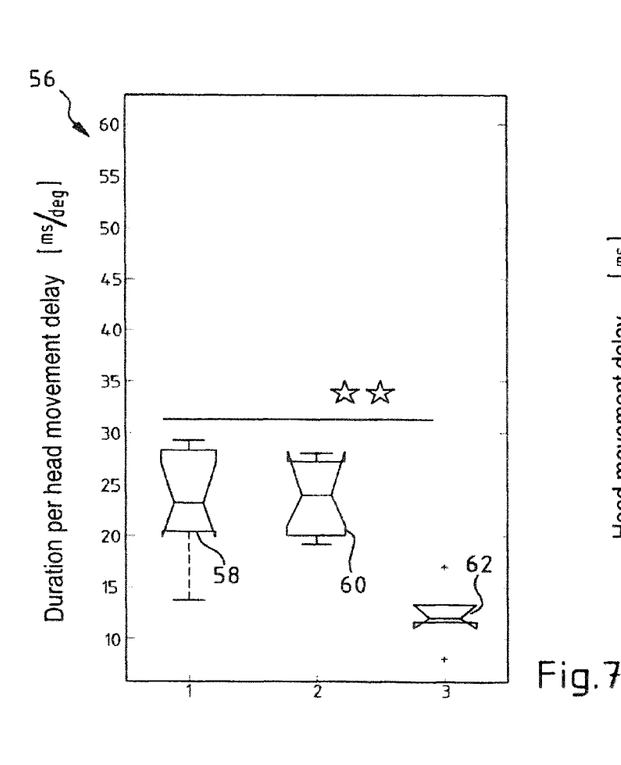
FIG. 7 is a diagram relating to statistical data regarding the movement periods, with respect to the movement length, of the head movement triggered by a visual stimulus in persons wearing progressive spectacles and persons who do not wear progressive spectacles.

FIG. 7 shows a diagram 56 with statistical data with respect to the movement duration $\Delta t$ of the head movement in ms with respect to the movement length of the head movement triggered by a visual stimulus 18 in persons who wear progressive spectacles and persons who do not wear progressive spectacles. The diagram 56 shows a distribution of the movement duration of the head movement of persons who do not wear progressive spectacles. Graph 58 visualizes a typical distribution of the movement duration of the head movement of persons who wear progressive spectacles with progressive lenses with weak addition. Graph 60 visualizes a typical distribution of the movement duration of the head movement of persons who wear progressive spectacles with progressive lenses with strong addition.

Figure 8:
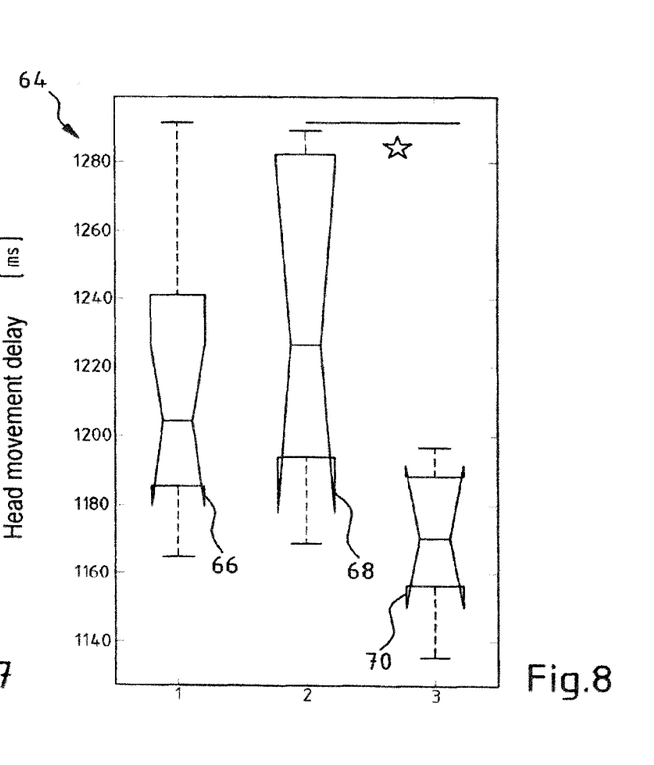
FIG. 8 is a diagram relating to statistical data regarding the delay of the head movement triggered by a visual stimulus in persons wearing progressive spectacles and persons who do not wear progressive spectacles.

FIG. 8 shows a diagram 64 with statistical data with respect to the delay in ms of the head movement triggered by a visual stimulus in persons who wear progressive spectacles and persons who do not wear progressive spectacles. Graph 66 shows a distribution of the delay of the head movement of persons who do not wear progressive spectacles. Graph 68 visualizes a typical distribution of the delay of the head movement of persons who wear progressive spectacles with progressive lenses with weak addition. The graph 70 in diagram 64 visualizes a typical distribution of the delay of the head movement in persons who wear progressive spectacles with progressive lenses with strong addition.

FIG. 5 to FIG. 8 show clearly that the head movement behavior for viewing with progressive spectacles which differs from the behaviour required for viewing without spectacles or viewing with single-focus spectacles is advantageous.

Figure 9:
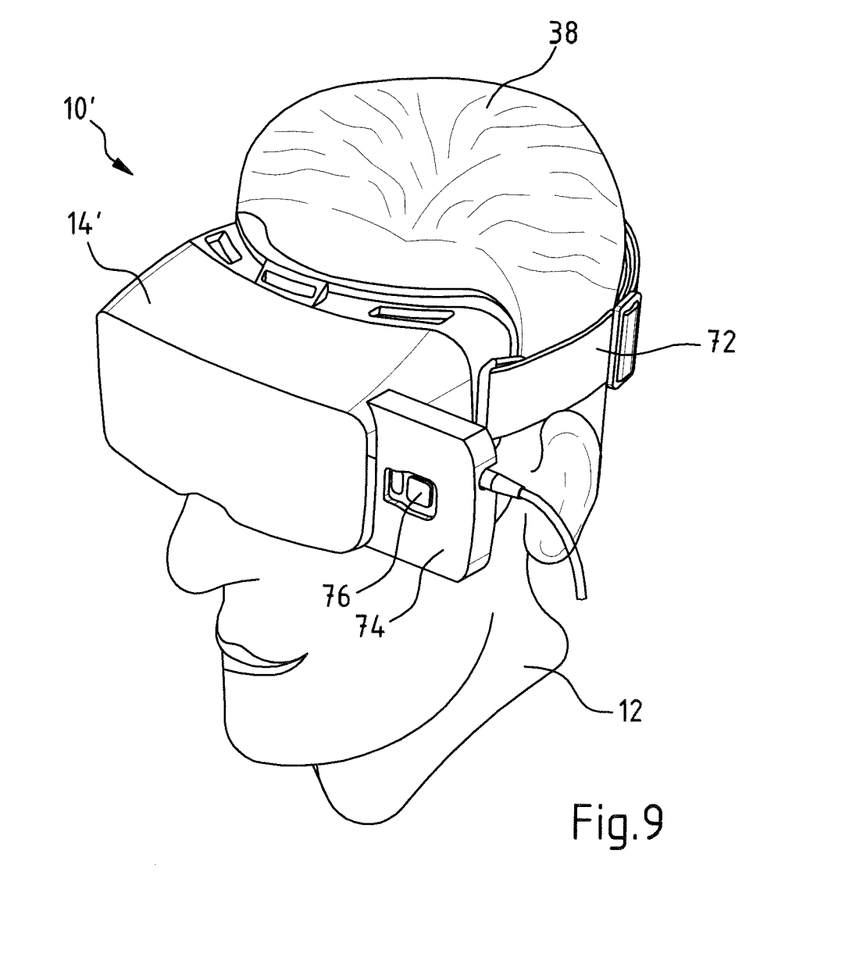
FIG. 9 is a second system for training head movements of a person.

FIG. 9 shows a second system 10' for training head movements of a person 12. Where modules and elements of the system 10' correspond to modules and elements of the system 10 which is described with reference to the previous figures, these are provided with identical numbers as reference signs.

The system 10' shown in FIG. 9 has, as a visual stimulus generation device, a head-mounted display (HMD) 14' with a support device 72 for holding a smart phone 74 on the head 38 of the person 12. An acceleration sensor 76 which is integrated in the smart phone 74 is used here as a measurement device 24 for capturing head movements of the person 12. For displaying visual stimuli and assessing the head movements of the person 12, the smart phone 74 contains a computer program which generates acoustic indication signals for the person 12.

Figure 10:
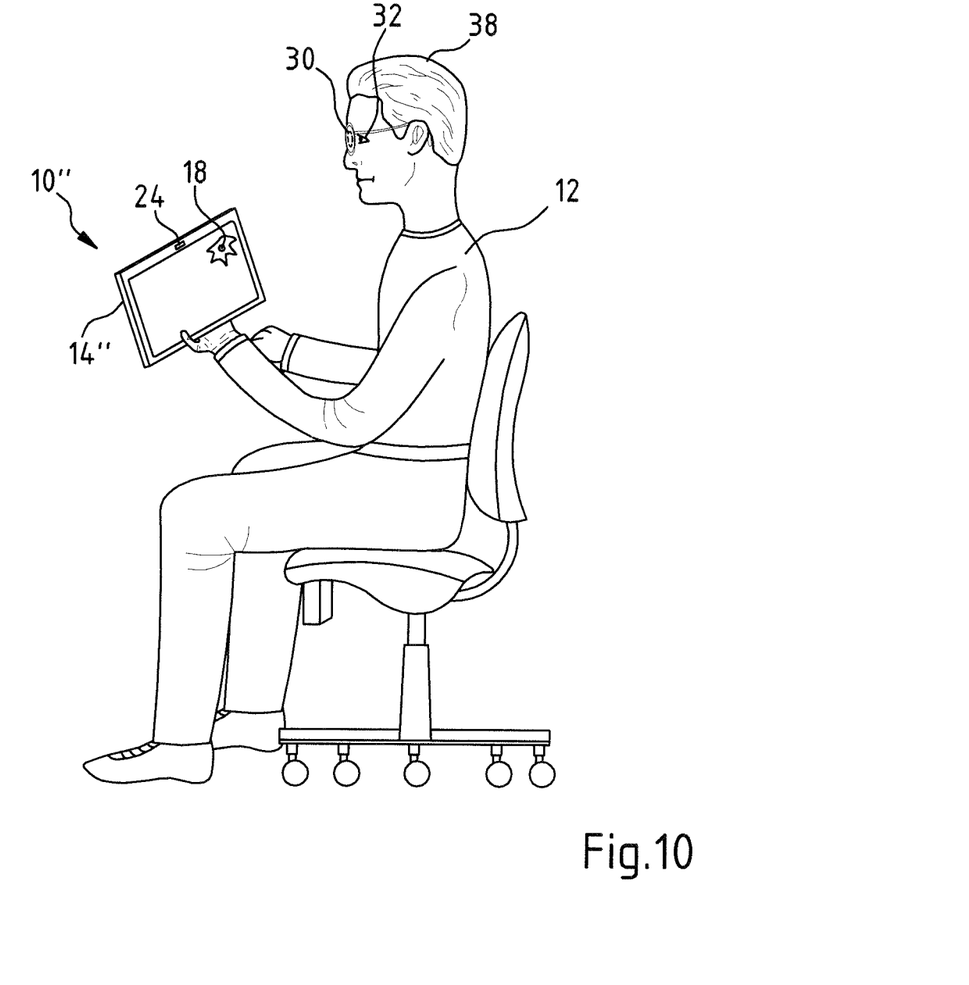
FIG. 10 is a third system for training head movements of a person.

FIG. 10 shows a third system 10" for training head movements of a person 12. Where modules and elements of the system 10" correspond to modules and elements of the system 10 which is described with reference to the previous figures, these are provided with identical numbers as reference signs.

System 10" for training head movements of a person 12, illustrated in FIG. 10, has a tablet PC 14" as a visual stimulus generation device. A camera, which interacts with an image evaluation routine in the tablet PC 14" and is integrated in the tablet PC, is used here as a measurement device 24 for capturing head movements of the person 12. For assessing the head movements of the person 12, the tablet PC 14" contains a computer program, which generates visual indication signals for the person 12 on the display of the tablet PC 14".

It should be noted that in an alternative embodiment of the previously described systems 10, 10', 10" for assessing head movements of a person 12, the measurement device 24 can also be designed for capturing the viewing directions of the left and the right eye 32, 32', wherein the assessment routine in the computational unit 16 permits assessment of the head movement and of the viewing directions of the person 12 for an individualized design of a progressive lens 39 which is adapted to the person 12.

In a system 10, 10', 10" according to the invention, provision may be made for feedback information to be indicated to the person 12 in the form of an acoustic signal or a visual signal, in particular in the form of an indication with a blurred image which, for example, corresponds to an unfavorable viewing direction through the progressive lens 39 of progressive spectacles and an unfavorable head posture. Such a system 10, 10', 10" can be used in particular for training head movements of a person 12 so that said person learns head movement behavior which is adapted to the progressive lenses 39 of progressive spectacles.

The visual stimulus 18 displayed on the visual stimulus generation device 14 can, in particular, also be a screen icon or an arrow symbol which signifies a sudden stop in a specific direction, or a symbol which is arranged eccentrically with respect to the center 22 of the screen by the visual stimulus generation device 14. However, the visual stimulus 18 can in principle also be a word or a letter or be in the form of a virtual reality which is displayed to the person 12 on a screen or using a HMD or with data spectacles. The visual stimulus 18 can here also be in the form of an interactive screen symbol which, as in a computer game or in a smart phone app, is displayed on a touch-sensitive screen and which can be activated with a specific head movement and/or viewing direction and/or specific combination of head movements and/or viewing directions.

In order to be used as feedback information, the assessment information in the computational unit 16 is computed with the assessment routine as far as possible in real time, wherein real time is understood in the present case to mean a time interval for capturing the head movement and ascertaining and outputting the assessment information, the length of which does not exceed 500 ms to 1 s. In principle, the system for training head movements of a person 12 can, however, also be used with computation times in which the ascertaining and outputting of the feedback information requires several seconds or even minutes.

In principle, the systems 10, 10', 10" described above enable a person 12 to start preparing for progressive spectacles in cases where the progressive spectacles have been optically configured, but not yet physically produced. The above-described systems 10, 10', 10" can, however, also be used to prepare a person 12 for progressive spectacles by way of the person 12 training on one of the previously described systems 10, 10', 10" and practicing viewing with progressive spectacles in alternation. In the process, a person 12 can learn head movements which take place earlier with respect to natural viewing without vision aid and can also learn head movements over a movement range which is greater than the head movements corresponding to natural viewing without vision aid. For this purpose, a person 12 can for example train several times a week for 5 to 15 minutes with a system 10, 10', 10" according to the invention in order to learn correspondingly modified head movement behavior. It should be noted, however, that in principle of course shorter or longer training times are also possible.

The previously described systems 10, 10', 10" are suitable for use by opticians and ophthalmologists. They provide a way in particular for finding out whether a person 12 will quickly take to wearing progressive spectacles. Moreover, the described systems 10, 10', 10" allow individualized optimization of the optical parameters of progressive lenses in progressive spectacles. It should be noted, however, that a previously described system 10, 10', 10" for training head movements of a person 12 can also be used as a physiotherapy training instrument, for example to treat neck and/or back pain, by way of causing the person 12 to move their head 38 more emphatically by way of displaying visual stimuli 18.

In summary, the following should be noted: The invention relates to a system 10, 10', 10" and to a method for training head movements of a person 12. Visual stimuli 18 are generated for the person 12 with a visual stimulus generation device. Head movements of the person 12 are captured with a measurement device 24. The head movement of the person 12 that is captured with respect to a generated visual stimulus 18 is assessed. Assessment information which is dependent on the assessment of the head movement captured with respect to a generated visual stimulus 18 is provided for the person 12 with an output device 36.

It is understood that the foregoing description is that of the preferred embodiments of the invention and that various changes and modifications may be made thereto without departing from the spirit and scope of the invention as defined in the appended claims.

LIST OF REFERENCE SIGNS

10, 10', 10" system
12 person
14 visual stimulus generation device
14' head-mounted display (HMD)
14" tablet PC
16 computational unit
18 visual stimulus
20 position 22 center
24 measurement device
26 camera
28 input interface
30, 30' center of rotation of the eye
32, 32' left and right eye
34, 35 coordinate system
36 output device
38 head
39 progressive lens
40, 48, 56, 64 diagram
42, 44, 46, 50,
52, 54, 58, 60,
62, 66, 68 graph
72 support device
74 smart phone
76 acceleration sensor

The invention claimed is:

1. A system to assist a person to adapt and train his or her head movement behavior, the system comprising:
    a visual stimulus generation device including a screen and being configured to generate a visual stimulus for a left and a right eye of the person on said screen with the left and right eyes having respective rotation points;
    a measurement device configured to capture a head movement of the person starting from a start head posture to an end head posture;
    an assessment device including a program code stored on a non-transitory computer readable medium for evaluating said head movement from the start head posture into the end head posture of the person to generate evaluation data directed to the head movement;
    said evaluation data being dependent upon the generated visual stimulus and upon the head movement detected in response to the generated visual stimulus;
    said program code including an evaluation routine configured to compare a first value for the head movement which is a desired value with respect to the generated visual stimulus to a second value for the head movement assigned to said visual stimulus wherein a displacement of the rotation points of the left and right eyes are captured in a person-specific coordinate system which is referred to a coordinate system of said visual stimulus generation device; and,
    an output device configured to provide the evaluation data for the person.

2. The system of claim 1, wherein said assessment device is configured as a computational unit which contains a computer program for assessing said head movement of the person that is captured by said measurement device with respect to said visual stimulus.

3. The system of claim 2, wherein said assessment device includes a non-transitory computer-readable medium and said computer program is stored in said non-transitory computer-readable medium.

4. The system of claim 2, wherein said computer program is configured to ascertain said assessment information by comparing said head movement captured by said measurement device with a predetermined head movement ascertained with respect to said visual stimulus and to output said assessment information to said output device.

5. The system of claim 4, further comprising:
    a non-transitory computer-readable medium having a data set stored therein; and,
    said computer program being configured to ascertain said predetermined head movement with respect to said generated visual stimulus by reading said data set stored in said non-transitory computer-readable medium.

6. The system of claim 4, wherein said computer program is configured to ascertain said predetermined head movement on the basis of a model which assigns a predetermined head movement to a visual stimulus.

7. The system of claim 6, wherein said model is configured to consider individual spectacle lens adaptation parameters for the person.

8. The system of claim 6, wherein said model is configured to consider at least one spectacle lens adaptation parameter from a group comprising frame dimensions, interpupillary distance, centration distance, corneal vertex distance, near reference point, distance reference point, refractive power, addition and width of the progression channel.

9. A non-transitory computer program medium with program code stored thereon for assessing head movements of a person on a computational unit in a system configured as claimed in claim 2.

10. The system of claim 1, wherein said visual stimulus generation device is adapted in the form of at least one of a screen, a head-mounted display (HMD), a tablet PC, a light source assembly, and a light pattern projection device.

11. The system of claim 1, wherein said measurement device includes at least one of a camera, a position sensor arranged on the head of the person, a solid angle sensor, and an acceleration sensor for capturing head movements.

12. The system of claim 1, wherein said assessment device is configured to at least one of provide an acoustic signal, provide a visual signal, provide a mechanical vibration signal for the person, and generate a virtual reality which is perceivable by the person.

13. A method for training head movements to assist a person to adapt, aid train his or her head movement behavior, the method comprising the steps of:
    providing a visual stimulus generation device having a screen;
    generating a visual stimulus on said screen for a left and right eye of the person with said visual stimulus generation device and with the left and right eyes having respective rotation points;
    capturing a movement of the head of the person from a start head posture into an end head posture in response to the generated visual stimulus;
    executing a program code stored on a non-transitory computer readable medium, the program code being for assessing the movement of the head of the person captured with respect to the generated visual stimulus;
    generating assessment information directed to the head movement with the assessment information being dependent upon the generated visual stimuli and upon the head movement detected in response to the visual stimuli;
    said program code including an evaluation routine configured to compare a first value for the head movement which is a desired value with respect to the generated visual stimulus to a second value for the head movement assigned to said visual stimulus wherein a displacement of the rotation points of the left and right eyes are captured in a person-specific coordinate system which is referred to a coordinate system of said visual stimulus generation device;
    and, providing the evaluation data for the person via an output device configured therefor.

14. The method of claim 13, wherein the assessment information is determined by comparing the captured movement of the head with a predetermined head movement ascertained with respect to the generated visual stimulus.

15. The method of claim 13, wherein the assessment information is provided in the form of at least one of an acoustic signal, a visual signal, a mechanical vibration signal, and a virtual reality.

16. A computer program product to assist a person to adapt and train his or her head movement behavior, the computer program product including program code stored on a non-transitory computer readable medium and being configured to perform a method comprising the steps of:

generating a visual stimulus for a left and right eye of the person with a visual stimulus generation device and with the left and right eyes having respective rotation points;

capturing a movement of toe head of the person from a start head posture into an end head posture in response to the venerated visual stimulus;

executing a program code stored on a non-transitory computer readable medium, the program code being for assessing the movement of the head of the person captured with respect to the generated visual stimulus;

generating assessment information directed to the head movement with the assessment information being dependent upon the generated visual stimuli and upon the head movement detected in response to the visual stimuli;

said program code including an evaluation routine configured to compare a first value for the head movement which is a desired value with respect to the generated visual stimulus to a second value for the head movement assigned to said visual stimulus wherein a displacement of the rotation points of the left and right eyes are captured in a person-specific coordinate system which is referred to a coordinate system of said visual stimulus generation device; and, providing the evaluation data for the person via an output device configured therefor.

17. A system to assist a spectacle wearer to learn to adapt and train his or her head movement behavior to progressive spectacles, the system comprising:

a visual stimulus generation device including a screen and being configured to generate a visual stimulus on said screen for a left and a right eye of the spectacles wearer with the left and right eyes having respective rotation points;

a measurement device configured to capture a head movement of the spectacles wearer from a start head posture to an end head posture;

an assessment device including program code stored on a non-transitory computer readable medium for evaluating said head movement from the start head posture into the end head posture of the person to generate evaluation data directed to the head movement;

said evaluation data being dependent upon the visual stimulus and upon the head movement detected in response to the generated visual stimulus;

said program code including an evaluation routine configured to compare a first value for the head movement which is a desired value with respect to the generated visual stimulus to a second value for the head movement assigned to said visual stimulus wherein a displacement of the rotation points of the left and right eyes are captured in a person-specific coordinate system which is referred to a coordinate system of said visual stimulus generation device; and, an output device configured to provide the evaluation data for the spectacles wearer so as to permit the spectacles wearer to learn how the spectacle wearer must change said head movement to see a clear picture through the spectacles.

* * * * *

UNITED STATES PATENT AND TRADEMARK OFFICE
CERTIFICATE OF CORRECTION

PATENT NO. : 10,335,025 B2  
APPLICATION NO. : 15/292949  
DATED : July 2, 2019  
INVENTOR(S) : Rifai et al.

Page 1 of 1

It is certified that error appears in the above-identified patent and that said Letters Patent is hereby corrected as shown below:

In the Specification

<u>In Column 5</u>:  
Line 18: delete "\t" and substitute -- $\Delta t$ -- therefor.

In the Claims

<u>In Column 11</u>:  
Line 16: delete "toe" and substitute -- the -- therefor.

<u>In Column 12</u>:  
Line 3: delete "spectacle wearer" and substitute -- spectacles wearer -- therefor.

Signed and Sealed this  
Third Day of December, 2019

Andrei Iancu  
*Director of the United States Patent and Trademark Office*